(12) United States Patent
Maget

(10) Patent No.: US 6,387,228 B1
(45) Date of Patent: May 14, 2002

(54) ELECTROCHEMICAL GENERATION OF CARBON DIOXIDE AND HYDROGEN FROM ORGANIC ACIDS

(76) Inventor: Henri J. R. Maget, 2661 Palomino Cir., La Jolla, CA (US) 92037

(*) Notice: Subject to any disclaimer, the term of this patent is extended or adjusted under 35 U.S.C. 154(b) by 14 days.

(21) Appl. No.: 09/631,168

(22) Filed: Aug. 3, 2000

(51) Int. Cl.$^7$ ................................. C25B 1/00
(52) U.S. Cl. ................ 204/230.2; 204/230.5; 204/278
(58) Field of Search ............... 204/230.2, 278, 204/230.5

(56) References Cited

U.S. PATENT DOCUMENTS

| | | | |
|---|---|---|---|
| 5,398,851 A | 3/1995 | Sancoff et al. | |
| 5,536,389 A | 7/1996 | La Naour et al. | |
| 5,971,722 A | 10/1999 | Maget et al. | |
| 6,010,317 A | 1/2000 | Maget et al. | |
| 6,267,864 B1 * | 7/2001 | Yadav et al. | 204/230.2 |

* cited by examiner

Primary Examiner—Arun S. Phasge
(74) Attorney, Agent, or Firm—Charles C. Logan II

(57) ABSTRACT

A device as described for the generation of high purity carbon dioxide (CO2) and hydrogen (H2) by electrochemical decomposition of aqueous solutions of liquid and solid organic acids. A d.c. power source is used to apply a preselected current to an electrochemical cell, consisting of an ion permeable membrane and two electrodes. The generation rate of CO2 and H2 is continuous and proportional to the applied current; it can be stopped instantaneously by interrupting the current. Small Battery operated generators can produce propellant CO2 and H2 to deliver fluids from containers. Other uses include the creation of anaerobic environments in incubation chambers.

41 Claims, 3 Drawing Sheets

FIGURE 1
FIGURE 2
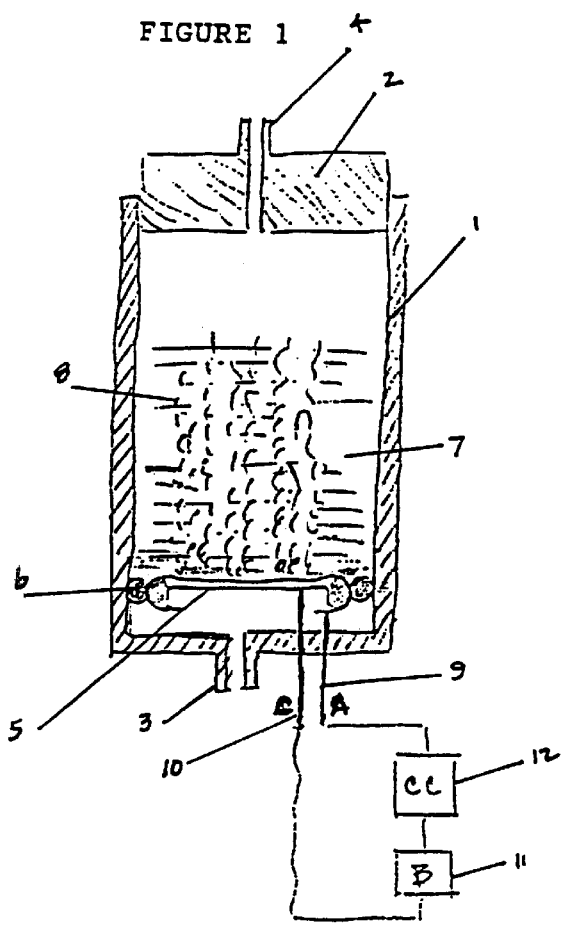
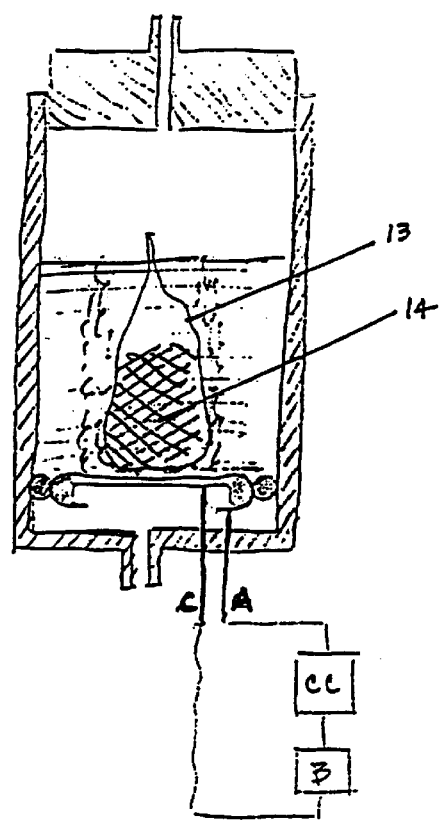

ELECTROCHEMICAL GENERATION OF CARBON DIOXIDE AND HYDROGEN FROM ORGANIC ACIDS

BACKGROUND OF THE INVENTION

The use of "in-situ" carbon dioxide generation, to deliver fluids is described in U.S. Pat. No. 5,398,851. In this instance, carbon dioxide is produced by chemical reaction of a sodium carbonate with an aqueous citric acid solution. These fluid delivery devices are rather inaccurate, mainly due to the difficulty to achieve and maintain a constant gas generation rate. Furthermore, their use is limited, since gas generation can not be controlled, varied or stopped.

Improvements over such devices are described in the Maget U.S. Pat. No. 5,971,722. In this instance the gas generator is electrochemically controlled and thereby achieves higher accuracy levels, without adding complexities or cost.

Commercial carbon dioxide gas generation systems, such as Becton-Dickinson's GasPak (tm), which are used in microbiology, are also based on the chemical reaction between sodium bicarbonate and citric acid.

In all instances, when carbon dioxide is generated by chemically reacting a metal (bi)carbonate with an acid, the reaction, once started is difficult to control, can not be conveniently stopped and at reaction completion residues containing chemicals, binders and additives are present, dissolved or in suspension in solution.

Hydrogen-driven fluid delivery is exemplified by the Disetronic Infuser disposable syringe pump, which uses a galvanic cell as a hydrogen source.

Commercial hydrogen gas generation systems, such as GasPak used in microbiology, are based on the chemical reaction of sodium borohydride with citric acid.

Again, these hydrogen generators are difficult to stop or to control to achieve a constant pre-set gas generation rate.

The present invention, based on selecting CO2 and H2 containing organic compounds, and an electrochemical decomposition process, results in the controlled generation of CO2 and H2, the rate being variable at will, which includes stops and restarts, and without formation of by-products.

The electrochemical cell, suitable for the practice of the present invention, is described in the Maget U.S. Pat. No. 6,010,317 and is hereby included by reference.

The organic acids suitable as sources of carbon dioxide, are of the family of mono- and polycarboxylated hydrocarbons, exemplified by formic acid, oxalic acid, tricarballylic acid, succinic acid, and the likes.

By applying energy, provided from an external d.c. power source, an anodic process strips hydrogen from the organic acid, releases hydrogen which is ionized and transported to the counterelectrode, while releasing carbon dioxide as the anodic product. In the instances when the organic acid only contains hydrogen and carbon dioxide, such as formic acid and oxalic acid, the anodic gas released during the process is mainly carbon dioxide, and the cathodic gas is mainly hydrogen. In this manner the CO2 and H2 generation rates are controlled by the applied current, and can thus be readily started, stopped or regulated.

SUMMARY AND OBJECTS OF THE INVENTION

It is the primary object of this invention to provide for a carbon dioxide generator which can be controllably operated.

It is another object of this invention to provide for a small, compact, self-contained, battery operated carbon dioxide generation apparatus.

It is the third object of this invention to provide carbon dioxide on demand, at a rate predictable from an applied current.

It is the fourth object of this invention to generate a high purity carbon dioxide.

It is a fifth object OF this invention to generate carbon dioxide without production of insoluble reaction by products.

The sixth to the tenth objects of this invention are similar to objects one to five, except that they are related to the generation of hydrogen.

These and other objects of the instant invention will become more apparent from the claims, specification, drawings and experiments.

DESCRIPTION OF THE DRAWINGS

FIG. 1 is the schematic drawing of a CO2 and H2 generator, using an aqueous solution of an organic acid (formic acid) as a CO2 ad H2 source;

FIG. 2 is a schematic illustration of the use of a solid organic acid (oxalic acid) contained in a porous, or water permeable, bag or pouch;

DESCRIPTION OF THE PREFERRED EMBODIMENT

Figure 3:
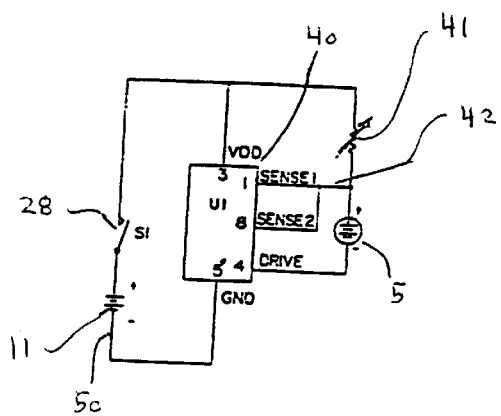
FIG. 3 is a schematic of the control circuitry of the generator.

The preferred embodiment consists of a container 1 enclosed by closure 2 with two outlets, 3 and 4. Within container 1 is located an electrochemical cell module 5 sealed by means of seal 6 to prevent fluid from leaking past module 5. The aqueous organic acid solution 7 is stored in an upper chamber in container 1 and is in contact with the anode 9 of cell module 5. Cathode 9 and anode 10 are connected to the power supply 11 and current controller 12. The dc power supply can be AC/DC converter or a battery.

The electronic circuit providing a constant current to electrochemical cell is illustrated in FIG. 3. A battery or AC/DC converter 11 supplies electric power to a constant current controller chip 40 such as Micronics Inc. precision current controller MX 963 or a TPS 7101 manufactured by Texas Instruments Corp. Controller chip 40 is connected to a load resistor 41 via sense leads 42. These leads provide feedback for the controlling chip 40 to sense the current passing through electrochemical cell 5. The output of current controlling chip 40 is thereafter connected to electrochemical cell 5 and returns to the power source via ground lead 50 thereby completing the circuit.

The other preferred embodiment illustrated in FIG. 2 is similar to the previous description, except that the organic acid 14 is a solid contained in a water permeable bag or pouch 13 made of natural or synthetic fiber or film. The purpose of the bag 14 is to prevent the solid organic acid 14 from forming a deposit on anode 9 thereby hindering the electrochemical process.

Figure 4:
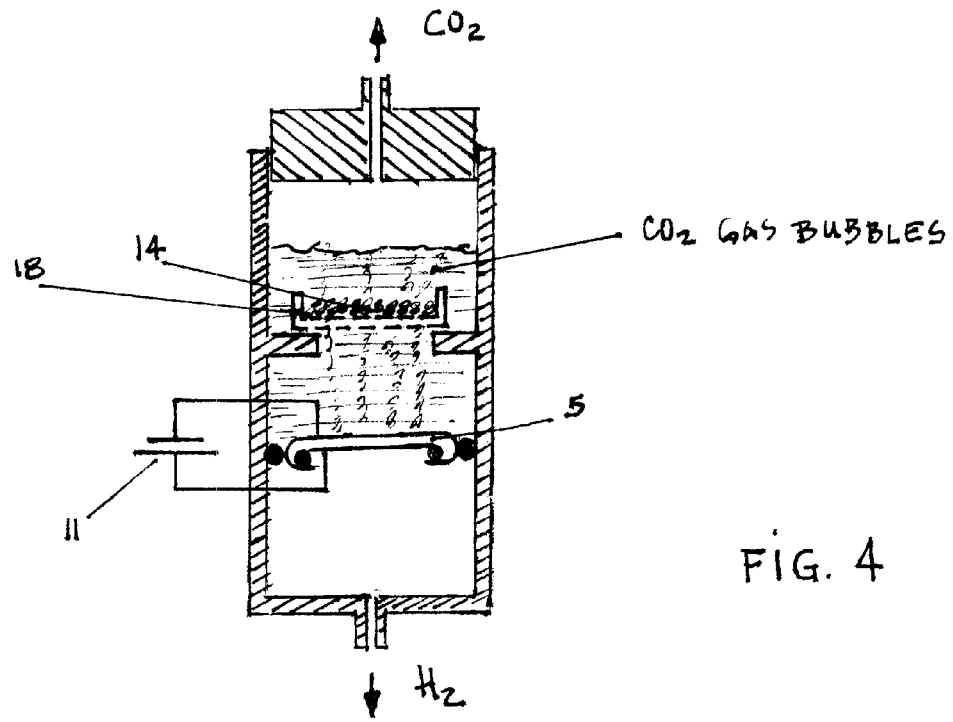
FIG. 4 is similar to FIG. 2 but shows the use of a grid/basket used to hold the solid acid.

Another embodiment similar to that illustrated in FIG. 2 is shown in FIG. 4. A metal, plastic or ceramic perforated basket or grid 18 is used to hold solid organic acid 14 which may be in the form of powder, granule or the like. Perforated basket or grid 18 functions to hold the solid acid to prevent formation of deposits on anode 9. It therefore prevents "fouling" of the electrode while still allowing the CO2 to escape. Illustrated is a battery operated unit. The battery can be external or an integral part of the system.

Figure 5:
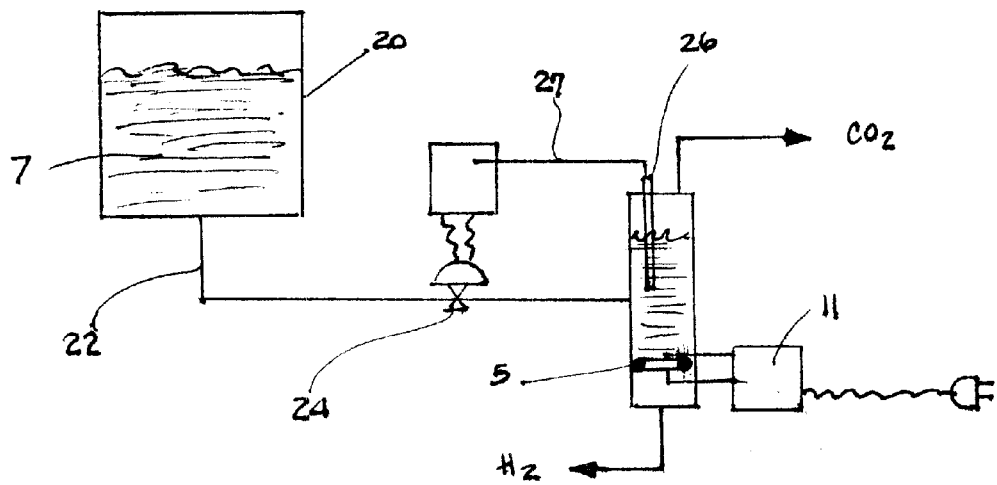
FIG. 5 is a schematic illustration of a continuous generator.

The embodiment illustrated in FIG. 5 shows a continuous generator that is line power operated. It has an organic acid storage tank 20. The acid 7 would flow through line 22 that has a valve 24 and on into container 1. The flow of acid is metered by means of a level sensor 26 that sends a signal through wire 27 to control unit 28 to open/close valve 24.

Figure 6:
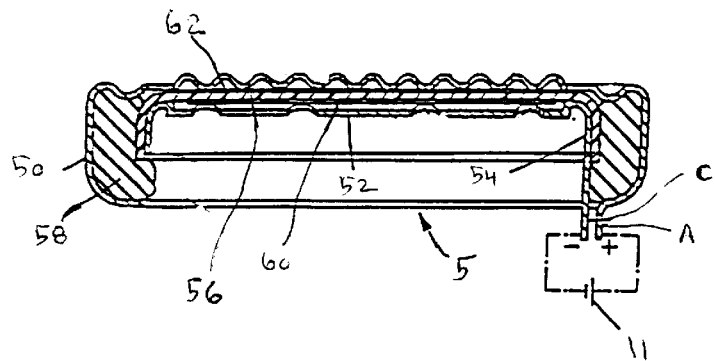
FIG. 6 is a sketch of the electrochemical cell module, used to decompose the organic acid.

The electrochemical cell module 5 is illustrated in FIG. 6 and its structure and manner of functioning are more thoroughly described in U.S. Pat. No. 6,010,317 which is incorporated by reference into this specification. The module 5 comprises four basic parts. The module parts are a first collector mounted at one end of an outer shell 50, a second current collector 52 mounted at one end of an inner shell 54, an ion exchange electrochemical cell 56 sandwiched between the current collectors, and a ring seal member 58. The electrochemical cell comprises an electrolytic membrane with electrodes 60 and 62 formed integrally on opposite sides of the membrane.

By activating switch 28, a current, the magnitude of which is set by variable resistor 41 is applied to e-cell module 5, thereby promoting the following reactions, when the organic acid is formic acid:

Anodic Reaction $$HCCOOH \rightarrow CO_2 + 2H^+ + 2e^- \tag{1}$$

Cathodic Reaction $$2H^+ + 2e^- \rightarrow H \tag{2}$$

The anodic reaction results in the stripping of carbon dioxide from the acid, generation of hydrogen, which is ionized and transported through the ion permeable membrane where it is released as hydrogen gas at the cathode.

Similarly, in the case of oxalic acid, the following reactions take place:

Anodic reaction:

$$\begin{array}{c} COOH \\ | \\ COOH \end{array} \longrightarrow 2\,CO_2 + 2\,H^+ + 2\,e^- \tag{3}$$

Cathodic Reaction $$2H^+ + 2e^- \rightarrow H_2 \tag{4}$$

However, in this instance, the ratio $CO_2/H_2=2$, as compared to a value of 1 for the formic acid decomposition process. Therefore, the current efficiency, i.e. moles of $CO_2$ produced/mA-hr is favorable for polycarboxylated acids such as oxalic acid.

In both instances, $CO_2$ bubbles 8 evolve from the anode and are evacuated via outlet 4. Hydrogen gas, formed at the cathode, is evacuated via outlet 3.

In some cases, the generation of hydrogen is beneficially used as an independent gas stream, or mixed with evolving $CO_2$ to create 50/50 $CO_2/H_2$ anaerobic gas mixture in the case of formic acid, or a 66.7/33.3 gas mixture in the case of oxalic acid.

Whenever hydrogen is not beneficially used, the cathode reaction can be mitigated by using an air depolarized cathode, i.e. supplying oxygen or air, to the cathode chamber, such that reactions (2) and (4) now become:

Air Depolarized Cathode Reaction

$$2H^+ + 2e^- + 1/2O_2 \rightarrow H_2O \tag{5}$$

and the electrochemical decomposition process results solely in the production of carbon dioxide and water.

During the electrochemical decarboxylation process, the concentration of the organic acid decreases progressively, resulting in a progressive increase of the e-cell voltage necessary to maintain a fixed current, i.e. a fixed CO2 and H2 generation rate. The cell voltage increase is the result of concentration polarization of the anode. Therefore, whenever a fixed voltage is applied to e-cell module 5, the rate of CO2 and H2 generation decreases progressively as the reaction proceeds, unless additional formic acid is provided to reinstate the initial concentration. However, in the case of a solid organic acid, the situation is different.

The solubility of oxalic acid in water is approximately 9.5 wt % at room temperature. If operating conditions, i.e. current applied to the e-cell module 5 is such that the dissolution rate of oxalic acid is greater than its consumption rate, the acid concentration remains constant at 9.5 wt % through-out the process, until the solid acid is totally consumed. Therefore, for self-contained systems, i.e. without the influx of additional acid, solid organic acids offer the opportunity to generate CO2 and H2 at a constant rate under operating conditions of an applied voltage instead of an applied current. This result is beneficially used whenever simple circuitry, i.e. only a resistor or potentiometer, is required for reasons of economy, while still a constant rate of CO2 and H2 generation is expected.

EXAMPLE I

A solution consisting of 6 mL of 88% formic acid and 14.4 mL of deionized water is electrically decomposed at 25–30° C., while a constant current of 80 mA is applied to the electrochemical cell. The CO2 and H2 generator is operated continuously for 77 hours. The average rate of gas generated at the anode during this time period is approximately 31.5 cc/hr. The gas composition of both anodic and cathodic streams is:

|  | Anodic gas composition | Cathode gas composition |
| --- | --- | --- |
| Carbon dioxide | 99.2 | 3.5 |
| Hydrogen | 0.3 | 95.7 |
| Oxygen | 0.3 | 0.8 |
| Carbon monoxide | ND | ND |
| ND = non detected | | |

EXAMPLE II 6.8 grams of oxalic acid, stored in a porous bag, are placed in 13.2 mL of deionized water. The current applied to the electrochemical cell is constant at 40 mA. The generator is operated continuously over a period of 87 hours. The average rate of gas generated at the anode is 33.8 cc/hr. The average rate of gas generated at the cathode is 16.6 cc/hr.

The gas composition of both anodic and cathodic streams is:

|  | Anodic gas composition | Cathodic gas composition |
| --- | --- | --- |
| Carbon dioxide | 99.1 | 4.0 |
| Hydrogen | 0.4 | 95.4 |
| Oxygen | 0.5 | 0.6 |
| Carbon monoxide | ND | ND |
| ND-non detected | | |

At the end of the test, the storage bag for the oxalic acid was visibly depleted of all solid acid.

EXAMPLE III

A saturated solution of oxalic acid in deionized water was electrochemically decomposed by applying a battery voltage supplied by two series-connected alkaline AA batteries. By manually changing the resistance from a variable resistor box, it was possible to change the current and voltage applied to the electrochemical cell. The following results were observed:

| Electrochemical cell voltage volts | Current flowing through the cell mA | Approximate gas generation rate at the anode, cc/hr |
| --- | --- | --- |
| 1.11 | 36.0 | 26.6 |
| 1.12 | 38.5 | 28.0 |
| 1.15 | 42.8 | 29.2 |
| 1.16 | 47.5 | 36.0 |

Although the preferred embodiments of this invention have been described by way of examples only, it will be understood that modifications may be made without departing from the scope of the invention, which is defined in the following claims.

What is claimed is:

1. Carbon dioxide generation apparatus comprising:
   a primary container having a top end, surrounding side walls having an interior surface, and a bottom end; means for closing said top end of said primary container;
   an electrochemical cell module having structure for decomposing an organic acid, said electrochemical cell module having a top surface, a bottom surface and a peripheral side edge; said electrochemical cell module being located in said primary container at a position spaced downwardly from said top and of said primary container;
   means sealing said peripheral side edge of said electrochemical cell module against said interior surface of said surrounding side walls of said primary container thereby forming an upper chamber in said primary container between said top surface of said electrochemical cell module and said means for closing said top end of said primary container;
   said electrochemical cell module having a cathode and an anode;
   a d.c. electrical power supply; and
   a primary electrical circuit connecting said anode and cathode to said d.c. electrical power supply to provide energy for generating carbon dioxide from an organic acid that would be placed in said upper chamber.

2. The apparatus of claim 1 wherein an aqueous solution of an organic acid is located in said upper chamber.

3. The apparatus of claim 2 wherein said organic acid is formic acid.

4. The apparatus of claim 2 wherein said acid is a monocarboxylic organic acid.

5. The apparatus of claim 2 wherein said acid is a polycarboxylic organic acid.

6. The apparatus of claim 1 wherein a solid organic acid is contained in a porous secondary container that is surrounded by a predetermined liquid in said upper chamber which produces an aqueous solution.

7. The apparatus of claim 6 wherein said solid organic acid is oxalic acid.

8. The apparatus of claim 6 wherein said porous secondary container is a bag made of natural fiber.

9. The apparatus of claim 6 wherein said porous secondary container is a bag made of synthetic fiber.

10. The apparatus of claim 6 wherein said porous secondary container is a bag made of a film material.

11. The apparatus of claim 6 wherein said porous secondary container is a perforated basket.

12. The apparatus of claim 6 wherein said porous secondary container is a perforated grid.

13. The apparatus of claim 1 further comprising means for automatically supplying organic acid to said primary container as demand requires.

14. The apparatus of claim 1 further comprising control means to control the carbon dioxide generation rate.

15. The apparatus of claim 14 wherein said control means comprises an electronic current controlling microchip.

16. The apparatus of claim 14 wherein said control means comprises a variable resistor in said primary electrical circuit.

17. The apparatus of claim 14 wherein said control means comprises an activating switch in said primary electrical circuit that can be opened to instantaneously halt the carbon dioxide production in said generation apparatus.

18. The apparatus of claim 1 further comprising means for evacuating carbon dioxide produced in said upper chamber.

19. The apparatus of claim 1 wherein said electrochemical cell module is spaced upwardly from said bottom end of said primary container and there are means for closing said bottom end of said primary container thereby forming a lower chamber below said bottom surface of said electrochemical cell module.

20. The apparatus of claim 19 further comprising means for evacuating hydrogen from said lower chamber.

21. The apparatus of claim 19 further comprising means for making said lower chamber accessible to air to depolarize said cathode and produce water as a bi-product in said lower chamber.

22. The apparatus of claim 1 wherein said d.c. electrical power supply is a battery.

23. The apparatus of claim 1 wherein said d.c. electrical power supply is a AC/DC converter.

24. Hydrogen generation apparatus comprising:
   a primary container having a top end, surrounding side walls having an interior surface, and a bottom end; means for closing said bottom end of said primary container;
   an electrochemical cell module having structure for decomposing an organic acid, said electrochemical cell module having a top surface, a bottom surface and a peripheral side edge; said electrochemical cell module being located in said primary container at a position spaced upwardly from said bottom end of said primary container;
   means sealing said peripheral side edge of said electrochemical cell module against said interior surface of said surrounding side walls of said primary container thereby forming a lower chamber in said primary container between said bottom surface of said electrochemical cell module and said means for closing said bottom end of said primary container; an upper chamber is formed in said primary container above said top surface of said electrochemical cell module;

said electrochemical cell module having a cathode and an anode;

a d.c. electrical power supply; and a primary electrical circuit connecting said anode and cathode to said d.c. electrical power supply to provide energy for generating hydrogen from an organic acid that would be placed in said upper chamber.

25. The apparatus of claim 24 wherein an aqueous solution of an organic acid is located in said upper chamber.

26. The apparatus of claim 25 wherein said organic acid is formic acid.

27. The apparatus of claim 25 wherein said acid is a monocarboxylic organic acid.

28. The apparatus of claim 25 wherein said acid is a polycarboxylic organic acid.

29. The apparatus of claim 24 wherein a solid organic acid is contained in a porous secondary container that is surrounded by a predetermined liquid in said upper chamber which produces an aqueous solution.

30. The apparatus of claim 29 wherein said solid organic acid is oxalic acid.

31. The apparatus of claim 29 wherein said porous secondary container is a bag made of natural fiber.

32. The apparatus of claim 29 wherein said porous secondary container is a bag made of synthetic fiber.

33. The apparatus of claim 29 wherein said porous secondary container is a bag made of a film material.

34. The apparatus of claim 24 further comprising control means to control the hydrogen generation rate.

35. The apparatus of claim 34 wherein said control means comprises an electronic current controlling microchip.

36. The apparatus of claim 34 wherein said control means comprises a variable resistor in said primary electrical circuit.

37. The apparatus of claim 34 wherein said control means comprises an activating switch in said primary electrical circuit that can be opened to instantaneously halt the hydrogen production in said generation apparatus.

38. The apparatus of claim 24 further comprising means for evacuating carbon dioxide produced in said upper chamber.

39. The apparatus of claim 24 further comprising means for evacuating hydrogen produced in said lower chamber.

40. The apparatus of claim 24 wherein said d.c. electrical power supply is a battery.

41. The apparatus of claim 24 wherein said d.c. electrical power supply is a AC/DC converter.

* * * * *